United States Patent [19]

Santus et al.

[11] Patent Number: 5,472,704
[45] Date of Patent: Dec. 5, 1995

[54] PHARMACEUTICAL CONTROLLED-RELEASE COMPOSITION WITH BIOADHESIVE PROPERTIES

[75] Inventors: Giancarlo Santus, Milan; Giuseppe Bottoni, Bergamo; Giovanni Sala, Verona, all of Italy

[73] Assignee: Recordati S.A., Chemical and Pharmaceutical Company, Chiasso, Switzerland

[21] Appl. No.: 174,191

[22] Filed: Dec. 27, 1993

Related U.S. Application Data

[63] Continuation of Ser. No. 832,229, Feb. 7, 1992, abandoned.

[30] Foreign Application Priority Data

May 30, 1991 [IT] Italy .................................. MI91A1486

[51] Int. Cl.⁶ .................................................. A61K 9/16
[52] U.S. Cl. .......................... 424/435; 424/473; 424/486; 424/487; 424/488
[58] Field of Search ..................................... 424/435, 419, 424/434, 493, 473, 494, 486, 487, 488

[56] References Cited

U.S. PATENT DOCUMENTS

| | | | |
|---|---|---|---|
| 3,699,963 | 10/1972 | Zaffaroni | 128/260 |
| 4,226,848 | 10/1980 | Nagai et al. | 424/78.05 |
| 4,713,243 | 12/1987 | Schiraldi et al. | 424/435 |
| 4,940,587 | 7/1990 | Jenkins et al. | 424/436 |
| 5,196,202 | 3/1993 | Konishi et al. | |

FOREIGN PATENT DOCUMENTS

| | | |
|---|---|---|
| 0205282 | 12/1986 | European Pat. Off. . |
| 0330532 | 8/1989 | European Pat. Off. . |
| 0387782 | 9/1990 | European Pat. Off. . |
| 0452268 | 10/1991 | European Pat. Off. . |
| 2497098 | 7/1982 | France . |
| 8502092 | 5/1985 | WIPO . |
| WO8502092 | 5/1985 | WIPO . |
| 8910117 | 2/1989 | WIPO . |

OTHER PUBLICATIONS

Patent Abstracts of Japan, vol. 12, No. 47, Feb. 12, 1988–Abstract of Japanese Appliction No. JP62195336.
Deutsche Apotheker Zeitung, vol. 130, No. 15, Apr. 12, 1990, pp. 791–801.
List, P. H. et al., Hagers Handbuch Der Pharmazeutischen Praxis, 1971, pp. 312–315.
Lehr et al., *J. of Controlled Release 13:* 1, 51–62, Jul., 1990.
An In–Vitro Investigation of Mucosa–Adhesive Materials for Use in Controlled Drug Delivery, Smart et al., *J. Pharm. Pharmacol.* 1984, 36:295–99.
In Vitro Method to Evaluate Bioadhesion of Microparticles, Sala et al., *Proceed. Intem. Symp. Control. Rel. Bioact. Mater.*, 16(1989), Controlled Release Society, Inc., pp. 420–421.
The Gastric Emptying of Hard Gelatin Capsules, Hunter et al., *International Journal of Pharmaceutics*, 17 (1983) 59–64.
Bioadhesion–Possibilities and Future Trends, Kellaway, Course No. 470, May 22–24, 1989.
Experimental Methods for Determination of Bioadhesive Bond Strength of Polymers with Mucus, Peppas et al., *S. T. P. Pharma* 5(3) 187–191, 1989.
R. Khosla et al., J. Pharm. Pharmacol. 39:47–49, 1987.

*Primary Examiner*—Thurman K. Page
*Assistant Examiner*—P. Kulkosky
*Attorney, Agent, or Firm*—Darby & Darby

[57] ABSTRACT

A pharmaceutical composition for the controlled release of medicinal drugs, which has the property of adhering to biologic tissues is described. The characteristic features of the composition are a plurality of small-size units capable of ensuring a gradual release of the active ingredient they contain the units being coated with a bioadhesive polymer layer. The composition makes it possible to keep the release controlling function separate from the function providing bioadhesion and can be adapted inter alia to oral, ocular, rectal, vaginal, nasal or periodontal administrations. An advantageous process for making the composition is also disclosed.

23 Claims, No Drawings

PHARMACEUTICAL CONTROLLED-RELEASE COMPOSITION WITH BIOADHESIVE PROPERTIES

This is a continuation of application Ser. No. 07/832,229, filed Feb. 7, 1992 now abandoned.

FIELD OF THE INVENTION

The present invention relates to a composition for the controlled release of medicinal drugs which has the additional property of adhering to biologic tissues, in particular to mucous membranes. The composition is designed for administration either by the oral route or other routes such as, for example, the nasal, rectal, vaginal, ocular and periodontal routes.

BACKGROUND OF THE INVENTION

The preparation of pharmaceutical compositions capable of ensuring a gradual and controlled release of active ingredients included therein has long been known to the pharmaceutical art. Known systems include tablets, capsules, microcapsules, microspheres and other dosage forms where the active ingredient is released gradually by various mechanisms.

These systems are intended to provide pharmaceutical dosage forms that can prolong the presence of the active ingredients in the subject to which they are administered at optimum plasma levels, thereby reducing the number of administrations required and improving patients' response to treatment.

It was recently observed that some drug bioavailability problems could be overcome by prolonging the presence of dosage forms at or near the locus within the host where their active ingredients are normally absorbed. These bioavailability problems stem from causes such as limited drug solubility (gastric or enteral), small absorption rate constant, or the presence of "windows" of absorption on ( i.e. a limited time of absorption which stops upon saturation). Examples of such drugs (without limitation) include (i) carbamazepine (an antiepileptic), furosemide (a diuretic), metoprolol (a beta blocker) and acyclovir (an antiviral). Other drugs for which benefit from prolonged presence at or near the locus of absorption in terms of their bioavailability characteristics include drugs that act specifically on the gastrointestinal tract (e.g. 5-aminosalyc acid) or which are absorbed most efficiently within the colon (e.g. peptides or proteins such as insulin, interferon, calcitonin, endorphins, human growth hormone, and various hormone growth factors).

From a theoretical point of view, an ideal solution of this problem can be found in formulation or dosage form materials with bioadhesive characteristics, bioadhesiveness being defined as the ability of a material (synthetic or biologic) to adhere to biologic tissues for a prolonged period of time. Although the length of this time cannot be given in terms of a numerical range that would apply to all drugs and all routes of administration, it is fair to describe such prolonged time period as a period of time (i) during which a drug is present at or near the locus of its absorption (ii) which is longer than the standard residence time for such drug (usually) not exceeding 8–10 hours for the gastrointestinal tract and up to about 24 hours).

In case of oral administration, normal or pathological stomach voiding and intestinal peristaltic movements may reduce the time for which a drug-releasing dosage form remains in contact with the mucous membrane responsible for absorption of the active ingredient. The rectal route of administration profits from the presence of the dosage form in the lower section of the rectum, where rectal veins make it possible to by-pass (and thereby overcome the effect of metabolism on the first passage through) the liver. Similar considerations apply to the ocular, vaginal, dental and nasal cavities, where spontaneous or ciliary movements may cause a premature elimination of a dosage form. The purpose of the bioadhesive is, therefore, to keep a pharmaceutical dosage form in an absorption site for an extended period of time. Naturally, release of effective amounts of the active ingredient must also be ensured throughout the bioadhesion period in order to attain this objective.

Some examples of bioadhesive materials used in controlled release formulations are already known.

International Patent Application No. WO 85/02092 discloses a bioadhesive pharmaceutical composition containing bioadhesive agents for skin and mucous membrane administration. The bioadhesive agents are fibrous, cross-linked and water-swelling polymers bearing carboxyl functional groups, which are, however, not water-soluble. This composition may consist of various dosage forms such as an "intimate mixture" of active ingredient and bioadhesive polymers, capsules, films or laminates. However, by the simple physical mixing process described in WO 85/02092 the active ingredient is simply dispersed in a bioadhesive polymer and the dispersion is placed in a capsule. There is no real bond between each drug-containing particle or granule and the bioadhesive substance and thus the contact area between active ingredient/bioadhesive and mucosa is always less than optimal, which causes clustering or clumping of the drug particles and the loss of the advantages imparted by the bioadhesive.

Another example is European Patent No. EP 205,282, which discloses a pharmaceutical controlled-release composition containing cellulose the composition being capable of adhering to mucous membranes. This composition is a solid dosage form and is confined to administration via the oral or nasal cavities. It consists of granules coated with mucoadhesive cellulose. These granules contain a pharmaceutical active ingredient, a long-chain aliphatic alcohol and water-soluble hydrous hydroxyalkylcellulose, the latter being used both as a granule ingredient and as a extra-granular ingredient. In other words, the same polymer (cellulose) that is a significant constituent of the matrix responsible for release control is also the material relied upon for bioadhesiveness.

A third example is found in U.S. Pat. No. 4,226,848, which discloses an administration method for a bioadhesive pharmaceutical composition. This method is said to ensure adhesion to the oral or nasal cavities of a pharmaceutical composition which includes a bioadhesive polymer matrix in which the active ingredient is suspended. In this case, the bioadhesive matrix is made up of both a cellulose ether and an acrylic acid homopolymer or copolymer.

Most of the above examples are characterized by the fact that release is controlled by means of the same material which ensures bioadhesion. This implies that, if bioadhesion characteristics are adjusted (for example by increasing or decreasing the amount of the bioadhesive material in the drug formulation), the release characteristics peculiar to a formulation will also be unintentionally affected and the effect may be undesirable (for example it might cause the rate of drug release to be faster or slower than would be appropriate). It is instead desirable to be able to manipulate dosage form adhesion while maintaining the release profile of the active ingredient(s) typical of a selected formulation and to modulate the release system in relation to the active ingredient while maintaining unchanged the bioadhesive properties of a formulation.

OBJECTS OF THE INVENTION

Accordingly, it is an object of the present invention to provide a controlled-release and bioadhesive pharmaceutical composition designed so that the function controlling release of the active ingredient(s) is independent of the function ensuring bioadhesion. It is thus possible to adapt (and optimize) the release-controlling function to any specific active ingredient and then, regardless of the nature of the active ingredient administered, to modulate bioadhesion to whichever extent best expresses the pharmacologic characteristics of the active ingredient, thus making it possible,for example, to increase the amount or to alter the type of bioadhesive without forcing a detrimental effect on the controlled-release characteristics.

The invention also allows appropriate modulation of the contact area between the locus of administration (e.g. mucous membrane) and the formulation so as to maximize bioadhesion and simultaneously increase the area available for drug absorption. The mass/exposed-surface ratio is much lower and more favorable to both release and adhesion than in the case of prior art tablets or large granules and, therefore, the contact surface between dosage form and locus of administration, which proportionally affects both bioadhesion and absorption, is very large.

These features of the composition which is an object of the present invention make it possible to administer the composition not only via the oral route, but—precisely due to the modulability of its components—also via the ocular, rectal, nasal, vaginal or periodontal routes, i.e. via any mucosa.

Another object of the invention is to provide an improved method for producing controlled-release drug compositions with bioadhesive properties.

SUMMARY OF THE INVENTION

In particular, the present invention is directed to a pharmaceutical composition which includes:

a) a multiplicity of microunits containing an active ingredient and at least one component which controls the release of the active ingredient in the environment of the use point for said composition, said component not substantially contributing to bioadhesive properties of said composition;

b) a coating for these microunits, comprising at least one bioadhesive material said coating being capable of ensuring adhesion of the microunits to the tissues or membranes of said use point; and, optionally;

c) an excipient which, depending on the route of administration selected, promotes delivery of the composition at the use point and/or permits retention of the pharmaceutical effectiveness of the composition during administration and at the use point.

Microunits which control release independently from the bioadhesive coating may comprise interchangeably controlled release matrices, reservoir or osmotic units, or biodegradable units. Advantageously, such units have an average diameter less than 1 mm.

The small size of the microunits affords a larger area of contact between the bioadhesive coating and the larger tissue. The controlled-release characteristics are adjusted, if need be, by choice of type and amount of intragranular controlled-release agent. Bioadhesiveness is adjusted by choice and amount of bioadhesive coating. If the bioadhesive coating impedes controlled-release, the intragranular controlled-release agent is changed to counteract such impedance.

Bioadhesive coatings may be selected from coatings comprising at least one of a large variety of bioadhesive polymers. It is possible to modulate the bioadhesion force either by adjusting the quantity of bioadhesive applied on the microunits or by using mixtures of different polymers with the desired combination of bioadhesive characteristics. Preferably, the coating envelops each individual microunit completely and is bonded thereto.

The choice of (extragranular) excipient depends on the administration route, the objective being to deliver the bioadhesive controlled release microunits to the use point in optimal manner. In the case of oral administration, such excipients are selected from components which favor a fast and/or broad distribution of the microunits on the mucous membrane, e.g. which avoid clustering, often caused by excessive and rapid swelling of the bioadhesive component due to a poor choice of extragranular excipient.

Another aspect of the invention is directed to a method for coating controlled-release microunits with bioadhesive polymers. The method comprises dry-compression tabletting without the aid of solvents and permits the quantity of bioadhesive combined with the microunits to be increased at will. It also permits coating of microunits with mixtures of polymers—bioadhesive or not—which could not be applied by conventional techniques.

DETAILED DESCRIPTION OF THE INVENTION

Controlled Release Microunits

The microunits a) which can be used for a controlled release of the drug include:

reservoir units matrix units osmotic units biodegradable units.

(a) Reservoir units (which involve an inert permeable membrane having specific diffusion characteristics which encases the active agent or a composition containing the active agent) are used when an essentially constant rate of release needs to be achieved over a prolonged period of time (accomplished through the provision within the reservoir of a saturated solution of the active agent) or when a first order release profile is desired (i.e. a decreasing rate of release caused by provision inside the unit of an unsaturated solution of the active agent).

(b) Matrix units (which involve active agents dispersed or dissolved uniformly throughout a rate-controlling polymer matrix) generally have complex release profiles depending on the amount of active agent imbedded therein the solubility of this agent to the fluid of the larger locus, the nature of the rate-controlling polymer (or polymers) and the geometry of the device. Choice of matrix units is thus more complex than that of reservoir units.

(c) Osmotic units (which generally involve tablets containing the active agent which in turn has a given osmotic pressure; the tablets are coated with a membrane semipermeable to the active agent and have a small hole drilled through the membrane) are chosen when delivery of a saturated solution of the active agent is desired at an essentially constant rate (until the drug solution inside the coated tablet is no longer saturated).

(d) Biodegradable units (matrix units containing dispersed active agent which is released via a slow degradation of the matrix) are chosen when, for example, solubility of the active agent into the polymer is very poor. The release characteristics of such units are determined by the points of the polymer matrix where hydrolytic degradation occurs, by whether degradation happens mostly or totally at the surface or mostly or totally uniformly throughout the matrix and by whether a diffusion system is superimposed on the matrix system.

These systems, which are used to control the release of the active ingredient, are thoroughly described in the literature and commonly used in the pharmaceutical art, and they are not in themselves an object of the present invention. A description of these systems can be found, for example, in the book by R. Baker: "Controlled release of biologically active agents", Ed John Wiley and Sons, New York, 1987, pp. 38–153 incorporated by reference. Such systems are also commercially available, e.g. from Stolle, R&D Corporation, Cincinnati, Ohio; or from Eurand Int'l S.p.A. Cinisello Balsamo, Milan, Italy.

The present invention permits selection, among various known systems, of the one which suits best the characteristics of the active ingredient to be administered and permits the system selected to be adapted to the peculiarities of the route of administration chosen. Such selection can readily be made by those of ordinary skill in the art. As a nonlimiting example, the release of a very soluble active ingredient can be slowed down to the desired rate by using a hydrophobic matrix as the release-controlling component, and the release of a scantily soluble active ingredient can be speeded up by use of an osmotic unit as the release-controlling component, in either case without fear of adverse effect on bioadhesion.

Whatever unit is selected for controlling release, it is desirable that its size be within the following limits: Preferred unit size may vary within the range from 125 to 600 microns. However, acceptable size range may vary from 1 to 2,000 microns, subject to optimization (well within the skill of the art) depending on the type of active ingredient to be administered, the use point, the type of unit chosen for administration and the excipients used.

Active Ingredients

A large number of active ingredients may be administered more effectively by means of the bioadhesive controlled-release composition of the present invention. In particular, administration of active ingredients requiring constant concentrations in the host is particularly advantageous when performed in accordance with this invention.

The active ingredients which can be used may be selected without limitation among those belonging to the following groups: analgesics, antibacterials, antibiotics, anticonvulsants, antidepressants, antidiabetics, antifungals, antihistaminics, antihypertensives, anti-inflammatories, antiparkinsonian drugs, antipyretics, anticholinergic drugs, antimicrobials, antiviral drugs, antiulceratives, bronchodilators, cardiovascular drugs, contraceptives, decongestants, diuretics, anti-hypoglycemics, hormones, ophthalmic drugs, hypnotics, sympathomimetic drugs, tranquilizers and vitamins.

Furosemide, terfenadine, calcitonin, pilocarpine, tetracycline and naproxen are only some examples of active ingredients which can be administered by means of compositions formulated in accordance with the invention. Again, the foregoing drugs are listed for illustrative purposes only; subject to individual optimization, the invention is applicable to bioadhesive pharmaceutical compositions regardless of the active ingredient or active ingredients incorporated therein.

Polymers with Bioadhesive Characteristics

In accordance with the present invention, the micro-units included in the pharmaceutical composition must be coated with bioadhesive polymers in order to interact with mucous membranes and adhere to them.

Many commercially available polymers already known in the literature (e.g., Smart, J. D. et al, *J.Pharm. Pharmacol.*, 1984, 36:295–99) as being bioadhesive can be used for this purpose. Examples (without limitation) include:

polyacrylic polymers such as, carhomer and carhomer derivatives (Polycarbophyl, Carbopol etc);

cellulose derivatives such as hydroxypropylmethylcellulose (HPMC), hydroxyethylcellulose (HEC), hydroxypropylcellulose (HPC) and sodium carboxymethylcellulose (NaCMC);

natural polymers such as gelatin, sodium alginate, pectin;

more generally, any physiologically acceptable polymer showing bioadhesive characteristics may be used successfully to coat controlled release units.

Bioadhesiveness can be determined in vitro, e.g. according to G. Sala et al., *Proceed Int. Symp. Contr. Release Bioact. Mat.*, 16: 420, 1989. See also WO 85/02092.

Suitable commercial sources for representative bioadhesive polymers include:

Carbopol acrylic copolymer - BF Goodrich Chemical Co., Cleveland, Ohio, USA.

HPMC - Dow Chemical Co., Midland, Mich., USA.

HEC (Natrosol) - Hercules Inc., Wilmington, Del., USA.

HPC (Klucel) - Dow Chemical Co., Midland, Mich., USA.

NaCMC - Hercules, Inc., Wilmington, Del., USA.

Gelatin - Deamo Chemical Corp., Elmford, N.Y., USA.

Sodium Alginate - Edward Mandell Co., Inc., Carmel, N.Y., USA.

Pectin - BDH Chemicals Ltd., Poole Dorset, UK.

Polycarbophil - BF Goodrich Chemical Co., Cleveland, Ohio, USA.

Although the weight ratio between controlled release units and bioadhesive polymer may vary between 5 and 0.1, the best results in terms of bioadhesive characteristics, low washability, and/or pharmaceutical properties and manufacturing technical and cost considerations are obtained with ratios of 2.5 to 0.25. While only one polymer may suffice for microunit coating, it was observed that, generally, a mixture of bioadhesive polymers with different characteristics yields better results. In particular, bioadhesive characteristics are more persistent when the coating is made of mixtures of acrylic polymers and cellulose derivatives.

Thus, for instance, mixtures of:

carbomer/hydroxypropyl-methylcellulose, polycarbophil/hydroxypropylmethyl-cellulose, or carbomer/hydroxypropylcellulose may be used to advantage in most administration situations.

Ratios between polymers showing more specific bioadhesive characteristics (e.g., an acrylic polymer) and any polymer acting at least predominantly as a binder (e.g., a cellulose derivative) may vary from about 0.2 to about 20. In most cases, optimum results are obtained using ratios of about 0.5 to about 5.

It should be noted that the final diameter of the coated particles may be from about 1 to about 2,500 microns, although it is generally preferable to limit the size to within the range of about 300 to about 600 microns.

Excipients

The excipients used to carry the pharmaceutical composition which is an object of the present invention in most of the customary routes of administration are those commonly known to the art. Examples can be found in Remington's 16th edition, Mack Publishing Co., Easton, Penna., 1980, p. 1355.

In particular, in case of administration by the oral route, the bioadhesive controlled-release microunits are preferably carried within a hard gelatin capsule or a tablet, made in accordance with known techniques. However, microunits are inclined to adhere to each other and lose a large share of their release (and adhesion) characteristics when hydration and swelling of the coating of the microunits contained in the composition start before the microunits come out of the capsule or are released following tablet disintegration. In such a case, the microunits behave as any common single-dose dosage form (capsule or tablet) which does not disintegrate rapidly. The advantage of a large contact surface between mucous membrane and dosage form, which is typical of the microunits, is thus lost (E. Hunter et al., Int. J. Pharm., 17: 59 (1983)).

A particular composition was developed to prevent this condition and thus keep the particles separated. This formulation permits (inter alia) an oral administration of the composition which is an object of the present invention without incurring the above problems.

Said formulation, which is also an aspect of the present invention, is characterized by the inclusion of the following substances among the ingredients of the composition:

a) a hydrophobic agent—such as, for instance, stearic acid and salts thereof such as magnesium stearate, calcium stearate, zinc stearate, talc, glyceryl fumarate, hydrogenated vegetable oils, polyethylene glycols, and other known compounds of similar behavior—which provide a protective coating on the bioadhesive particles thus delaying particle coating hydration;

b) a strong disintegrating agent which will speed up the exit of the microunits from the capsule or the disintegration of the tablet, and ensure dispersion of the bioadhesive microunits on the gastrointestinal mucous membrane.

Disintegrating agents include without limitation commercially available cross-linked polyvinylpyrrolidone, sodium carboxymethylstarch, sodium croscarmellose, starch, alginic acid, calcium carboxymethylcellulose, Guar gum, silicon dioxide, sodium alginate, and other known compounds of similar behavior.

The weight percentage in a formulation to be administered by the oral route may vary from about 1 to about 10% for the hydrophobic ingredient and from about 2 to about 20% for the disintegrating agent. Percentages are by weight based on the weight of the finished product.

Microunit Coating Method

There are two known processes for combining bioadhesive polymers and the active ingredient: mixing of polymers and the active ingredient and spray coating of the active ingredient in a fluid bed. However, these processes show various disadvantages when used to coat the microunits referred to in the present invention. Mixing will not permit individual coating of particles containing the active ingredient and will not provide sufficient force to firmly bind the coating to the microunits. Spray coating in a fluid bed involves excessively long processing times when the quantity of coating to be laid on the active ingredient-containing particle is high and, furthermore, it does not permit use of polymer mixtures if the constituent polymers of the mixture are only soluble in different solvents.

It has now been found, and this is also an aspect of the present invention, that a dry-tabletting method will permit the effective coating of microunits with bioadhesive polymers substantially free of one or both of the foregoing disadvantages.

According to this method, the microgranules are intimately mixed (using, e.g., a TURBULA mixer) with a bioadhesive polymer or with a mixture of polymers, including at least one bioadhesive polymer, and then compressed. The mass obtained by compression is then crumbled (e.g. by granulation) and the bioadhesive coated granules are sieved to obtain particles of the required size. Compression may be accomplished by any suitable means that would cause the bioadhesive coating to bind to the controlled-release microunit surface, such as a tabletting machine, or a compaction mill. The compression force used should preferably be the minimum required to bind the bioadhesive to the controlled-release microunit surface, but this is readily determined by those skilled in the art using no more than routine experiment. Usually, minimal average compression force values are within the range of about 0.5 to about 1KN. As shown in the examples below, increase of the compression force does not affect the properties of the present invention.

A microscopic examination will show that all the microunits coated by the dry-compression method described above are individually and thoroughly coated with bioadhesive polymers.

Another advantage of this method is that the compression force and subsequent crumbling do not significantly affect the desirable release characteristics of the bioadhesive granules. This makes the method flexible. The method is also suitable for use with a wide variety of materials and active ingredients.

By this method, it is, for instance, easy to coat even single i.e. individual microunits with relatively large quantities of bioadhesive polymer (e.g.,up to ten times of the weight of the "naked" controlled-release microunit) that can be compression-bound to the surface. Since increasing the quantity of a bioadhesive polymer will increase the strength of bioadhesion, it is possible to modulate total dosage form adhesion and adapt it in a simple and economic way to the requirements of the drug to be administered. If the amount and nature of the bioadhesive coating is such that it will impede release rate, a faster release unit can be provided to perform the release control function.

The following examples will describe the invention and its advantages without limiting the scope of the invention in detail, in particular with regard to the materials, techniques and active ingredients used.

The examples were carried out using the following equipment: TURBULA® mixer (Willi A. Bachofen AG Basel, Switzerland), TONAZZI® kneader (Tonazzi vittorio e C. srl, Milan, Italy), ERWEKA® granulator (Erweka GmbH Heusenstamm, Germany), SILVERSON® turboemulsifier (Silverson Ltd., Chesham, U.K.), Cinisello Balsamo, Milan, Italy) WURBTER-GLATT® fluid-bed system (Glatt GmbH Binzen-Lorrach, Germany).

EXAMPLE 1

Bioadhesive Granules With Matrix Units for the Controlled Release of Furosemide a) Hydrophobic Matrix Obtained by Granulation with Melted Excipients 50 parts of furosemide are mixed with 25 parts of hydrogenated castor oil and the resulting mixture is kneaded using 25 parts of melted hydrogenated castor oil as a granulation fluid. The resulting mixture is then granulated to obtain granules with a diameter of 125 to 500 microns. 33 parts of the granules obtained are mixed with 33 parts of an acrylic copolymer (Carbopol® 934 - Goodrich Chemical Co.) and 33 parts of hydroxyproprylmethylcellulose with a viscosity of 4000 cps in 2% water solution (Methocel® E4M - Dow Chemical Co.). The mixture is then tabletted in an eccentric press using a compression force of 8 KiloNewtons (KN), obtaining tablets with a diameter of 21 mm. The tablets are then crumbled and sieved so as to obtain granules with a diameter of 300 to 600 microns.

b) Matrix With Intermediate Hydrophobicity Obtained by Granulation With Melted Excipients 25 parts of furosemide are mixed with 25 parts of hydrogenated castor oil and 25 parts of calcium phosphate. The mixture is kneaded using 25 parts of melted hydrogenated castor oil as a fluid binder. The resulting mixture is then granulated to obtain granules with a diameter of 125 to 500 microns. 33 parts of the granules obtained are mixed with 33 parts of an acrylic copolymer (Carbopol® 934 - Goodrich Chemical Co.) and 33 parts of hydroxyproprylmethylcellulose with a density of 4000 cps (Methocel® E4M - Dow Chemical Co.). The mixture is then tabletted in an eccentric press using a compression force of 8 KN, obtaining tablets with a diameter of 21 mm. The tablets are then crumbled and sieved so as to obtain granules with a diameter of 300 to 600 microns.

EXAMPLE 2

Bioadhesive Granules with Reservoir Units For the Controlled Release of Furosemide a) Reservoir Unit with a 0.5 Nucleus/ Bioadhesive-Polymer Ratio 50 parts of furosemide are kneaded with 47.5 parts of lactose and 2.5 parts of a 10% aqueous solution of polyvinyl alcohol as a fluid binder. The resulting mixture is then dried in a forced ventilation oven at 50° C. for 3 hours and granulated to obtain granules with a diameter of 125 to 600 microns. The controlled release of the active ingredient is achieved by coating 85 parts of the granules obtained in a fluid-bed system using as a coating agent 15 parts of a polymer film which has the following composition:

| | |
|---|---|
| glyceryl monostearate | 13.50 (parts) |
| beeswax | 1.20 |
| stearyl alcohol | 0.15 |
| cetyl alcohol | 0.15 |

33 parts of the granules so coated are mixed with 33 parts of Carbopol® 934 and 33 parts of Methocel® E4M. The mixture is then tabletted in an eccentric press using a compression force of 8 KN, obtaining tablets with a diameter of 21 mm. The tablets are then crumbled and sieved so as to obtain granules with a diameter of 300 to 600 microns.

b) Reservoir Unit With a Nucleus/Bioadhesive-Polymer Ratio of 0.25

Bioadhesive granules containing furosemide in reservoir nuclei are prepared in accordance with the method described in Example 2a), as far as the release-controlling nucleus is concerned. 20 parts of granules so prepared and coated are mixed with 40 parts of Carbopol® 934 and 40 parts of Methocel® E4M. The mixture is then tabletted in an eccentric press using a compression force of 8 KN, obtaining tablets with a diameter of 21 mm. The tablets are then crumbled and sieved so as to obtain granules with a diameter of 300 to 600 microns.

EXAMPLE 3

Bioadhesive Granules With Reservoir Units for the Controlled Release of Terfenadine a) Reservoir Nucleus With Low Hydrophilic Properties 50 parts of terfenadine are mixed with 47 parts of calcium hydrogen phosphate. The mixture is kneaded using 3 parts of a 10% aqueous solution of polyvinyl alcohol as a fluid binder. Mixture processing, granulation, granule coating with a film capable of controlling the release and further coating with Carbopol 934 and Methocel® E4M, follow the method described in Example 2a). Here again granules with a diameter of 300 to 600 microns are obtained.

b) Reservoir Nucleus With High Hydrophilic Properties 50 parts of terfenadine are mixed with 47 parts of lactose. The mixture is kneaded using 3 parts of a 10% aqueous solution of polyvinyl alcohol as a fluid binder. Mixture processing, granulation and granule coating with a film capable of controlling the release follow the method described in Example 2a). 50 parts of the granules so coated are mixed with 25 parts of Carbopol® 934 and 25 parts of Methocel® E4M. The mixture is then tabletted in an eccentric press using a compression force of 8 KN, obtaining tablets with a diameter of 21 mm. The tablets are then crumbled and sieved so as to obtain granules with a diameter of 300 to 600 microns.

c) Reservoir Nucleus with Intermediate Hydrophilic Properties 50 parts of terfenadine are mixed with 27 parts of calcium hydrogen phosphate and 20 parts of lactose. The mixture is kneaded using 3 parts of a 10% aqueous solution of polyvinyl alcohol as a fluid binder. Mixture processing, granulation and granule coating with a film capable of controlling the release follow the method described in Example 2a). 33 parts of the granules so coated are mixed with 33 parts of Carbopol® 934 and 33 parts of Methocel® E4M. The mixture is then tabletted in an eccentric press using a compression force of 8 KN, obtaining tablets with a diameter of 21 mm. The tablets are then crumbled and sieved so as to obtain granules with a diameter of 300 to 600 microns.

EXAMPLE 4

Bioadhesive Granules with Biodegradable Units for the Controlled Release of Calcitonin An aqueous solution is prepared with 50 parts of calcitonin and 50 parts of albumin. This solution is then emulsified in cotton-seed oil with the aid of sorbitan trioleate (Span® 85 available from ICI Imperial Chemical Industries). A fine and homogeneous dispersion of the aqueous phase in the fatty phase is obtained using a turboemulsifier. 2,3-butanedione is then added to the emulsion to permit albumin cross-linking. This emulsion is then repeatedly diluted with ether to replace most of the fatty phase. The microcapsules so obtained are collected by centrifugation and dried. 33 parts of these microcapsules are mixed with 33 parts of Carbopol® 934 and 33 parts of Methocel® E4M. The mixture is then tabletted in an eccentric press using a compression force of 1.5 KN, obtaining tablets with a diameter of 21 mm. The tablets are then crumbled and sieved so as to obtain granules with diameters of 100 to 200 microns.

EXAMPLE 5

Bioadhesive Granules with Osmotic Units for the Controlled Release of Naproxen 50 parts of naproxen are kneaded with 47.5 parts of mannitol and 2.5 parts of a 10% aqueous solution of polyvinyl alcohol as a fluid binder. The mixture so obtained is then dried in a forced ventilation oven at 50° C. for 3 hours and granulated to obtain granules with a diameter of 125 to 600 microns. In order to control naproxen release, the nuclei are coated with a semi-permeable membrane, which is made porous by the presence of water-soluble material (polyethylene glycol). 85 parts of granules are coated in a fluid bed system using as a coating agent 15 parts of a polymer film with the following composition:

| | |
|---|---|
| cellulose acetate | 90 parts |
| polyethylene glycol | 10 parts |

33 parts of the granules so coated are mixed with 33 parts of Carbopol® 934 and 33 parts of Methocel® E4M. The mixture is then tabletted in an eccentric press using a compression force of 8 KN, obtaining tablets with a diameter of 21 mm. The tablets are then crumbled and sieved so as to obtain coated granules with a diameter of 300 to 600 microns.

EXAMPLE 6

Bioadhesive Granules with Biodegradable Units For the Controlled Release of Tetracycline Hydrochloride 30 parts of tetracycline hydrochloride and 70 parts of poly(L-lactate/glycolate) (1/1) copolymer are dispersed by stirring in dichloromethane. This dispersion is emulsified in a 4% aqueous solution of polyvinyl alcohol in a turboemulsifier. The use of a turboemulsifier permits microcapsules of adequately small size to be obtained. The vessel containing the emulsion is set at 37° C. for 4 hours in order to allow evaporation of dichloromethane. During this operation, the emulsion is constantly stirred. After 4 hours, the microcapsules are separated by filtration, washed in cold water and then dried in an air circulating oven at 40° C. for 24 hours. 50 parts of the microcapsules are mixed with 25 parts of Carbopol® 934 and 25 parts. of Methocel® E4M. The mixture is then tabletted in an eccentric press using a compression force of 1.5 KN, obtaining tablets with a diameter of 21 mm. The tablets are then crumbled and sieved so as to obtain coated granules with a diameter of 50 to 200 microns.

EXAMPLE 7

Bioadhesive Granules with Biodegradable Units For the Controlled Release of Pilocarpine 5 parts of pilocarpine and 95 parts of poly(L-lactate/glycolate) (1/1) copolymer are dispersed in dichloromethane by constant stirring. This dispersion is then emulsified in a 4% aqueous solution of polyvinyl alcohol. Stirring is adjusted so as to obtain a very fine and homogeneous dispersion of the organic phase in the aqueous phase. The emulsion is then placed in a temperature-controlled bath set at 37° C. and stirred for 4 hours in order to let all the dichloromethane evaporate. After cooling, the microcapsules are separated by filtration and washed with cold water. The washed microcapsules are dried for 24 hours in an air circulating oven at 40° C. 50 parts of the microcapsules so obtained are mixed with 25 parts of Carbopol® 934 and 25 parts of Methocel® E4M. The mixture is then tabletted in an eccentric press using a compression force of 1.5 KN, obtaining tablets with a diameter of 21 mm. The tablets are then crumbled and sieved so as to obtain granules with a diameter smaller than 10 microns.

EXAMPLE 8

Release of Granules from a Hard-Gelatine Capsule for Oral Administration

This example emphasizes the role played by the excipients (disintegrating agent and hydrophobic agent) added to a composition for oral administration. Various formulations were tested in order to evaluate the efficacy of various disintegrating agents combined with magnesium stearate.

A hard-gelatine capsule No. 3 containing the bioadhesive controlled release granules (containing furosemide and prepared as described in Example 1 a)) and the other excipients is held on the bottom of a dissolution vessel filled with 37° C. water and stirred by rotating at 20 rpm. The capsule is removed from the vessel at pre-established intervals and the water is filtered in order to recover any released granules. The exact quantity of granules released is determined by assaying the active ingredient.

Capsule A
Bioadhesive controlled-release granules without excipients.

Capsule B
95 parts of bioadhesive controlled-release granules and 5 parts of magnesium stearate.

Capsule C
95 parts of bioadhesive controlled-release granules and 5 parts of croscarmellose sodium.

Capsule D
90 parts of bioadhesive controlled-release granules, 5 parts of magnesium stearate and 5 parts of oroscarmellose sodium.

Capsule E
85 parts of bioadhesive controlled-release granules, 5 parts of magnesium stearate and 10 parts of croscarmellose sodium.

Capsule F
80 parts of bioadhesive controlled-release granules, 5 parts of magnesium stearate and 15 parts of croscarmellose sodium.

Capsule G
90 parts of bioadhesive controlled-release granules, 5 parts of magnesium stearate and 5 parts of cross-linked polyvinylpyrrolidone.

Capsule H
85 parts of bioadhesive controlled-release granules, 5 parts of magnesium stearate and 10 parts of cross-linked polyvinylpyrrolidone.

Capsule I
90 parts of bioadhesive controlled-release granules, 5 parts of magnesium stearate and 5 parts of carboxymethylstarch.

TABLE 1

| Time  | % Granules Released |     |     |     |     |     |     |     |     |
|-------|-----|-----|-----|-----|-----|-----|-----|-----|-----|
| (min) | A   | B   | C   | D   | E   | F   | G   | H   | I   |
| 2     | 0   | 0   | 0   | 0   | 0   | 0   | 0   | 20  | 0   |
| 5     | 0   | 0   | 0   | 0   | 10  | 50  | 0   | 80  | 0   |
| 10    | 0   | 5   | 5   | 15  | 30  | 65  | 20  | 100 | 5   |
| 15    | 0   | 5   | 10  | 20  | 35  | 75  | 30  | 100 | 5   |
| 20    | 0   | 15  | 15  | 35  | 50  | 80  | 70  | 100 | 15  |
| 25    | FOC | 40  | 30  | 75  | 85  | 90  | 100 | 100 | 50  |
| 30    | FOC | 50  | 50  | 95  | 95  | 100 | 100 | 100 | 85  |
| 35    | FOC | 50  | 60  | 100 | 100 | 100 | 100 | 100 | 100 |

"FOC" means formation of clumps, evaluated by visual inspection.

The figures shown in Table 1 evidence that the simultaneous presence in the capsule, together with the bioadhesive controlled release granules, of a hydrophobic agent and a disintegrating agent can speed up the exit of the granules (capsules D–I). The presence of a hydrophobic agent alone (capsule B) or a disintegrating agent alone (capsule C) is not sufficient to cause all the bioadhesive granules to come out of the capsule within the period of time considered appropriate (0– 35 min). The example combination showing the best results is that of capsule H, but capsules D through I and especially capsules E–H gave excellent results.

EXAMPLE 9

Bioadhesive Composition for the Controlled Release of Pilocarpine in the Eye 60 parts of bioadhesive granules for the controlled release of pilocarpine, which are prepared as described in Example 7, are dispersed in 40 parts of a saline isotonic solution immediately before instillation. The isotonic suspension is instilled into the eye. The results will show prolonged release of pilocarpine compared to non-bioadhesive formulations.

EXAMPLE 10

Bioadhesive Composition for the Controlled Release Of Calcitonin in the Nasal Cavity 65 parts of bioadhesive granules for the controlled release of calcitonin, which are prepared as described in Example 4, are dispersed in 35 parts of a 2% aqueous solution of polyvinylpyrrolidone immediately before instillation. The resulting suspension is instilled into the nasal cavity. The results will show prolonged release of calcitonin compared to conventional formulations.

EXAMPLE 11

Bioadhesive Composition for the Controlled Release of Tetracycline Hydrochloride in the Periodontal Cavity 23 parts of bioadhesive granules for the controlled release of tetracycline, which are obtained as described in Example 6, are mixed with 2 parts of tetracycline hydrochloride. This antibiotic fraction will provide a readily soluble dose. The mixture of bioadhesive granules and free tetracycline hydrochloride is mixed with 75 parts of 35% poloxamer gel. The gel containing bioadhesive granules and free tetracycline is injected into the periodontal cavity by a syringe equipped with a suitable needle. The results will show prolonged release of tetracycline compared to conventional formulations.

EXAMPLE 12

Bioadhesive Composition for the Controlled Release of Naproxen in the Vagina or in the Rectum 25 parts of bioadhesive granules for the controlled release of naproxen, which are obtained as described in Example 5, are dispersed in 75 parts of mygliol® 810 (a hydrophobic liquid vehicle available from Dynamit Nobel Aktieng. 5 Cologne 80 Wiener platz Germany) and stirred for 15 minutes in a stainless steel reactor. The following compounds which make up the shell are placed in another stainless steel vessel: gelatine 65 parts, glycerin 33 parts, titanium dioxide 1 part, sodium methylparaoxybenzoate 0.5 parts and sodium propylparaoxybenzoate 0.5 parts. These compounds are melted at 70° C. and stirred for 15 minutes. The melted shell mixture is introduced into a Scherer® capsule filling machine. Soft gelatine capsules of appropriate shape and size are produced and the dispersion of bioadhesive granules in mygliol® 810 is injected into the suppositories by means of suitable needles. The results will show prolonged release of naproxen compared to commercially available formulations.

EXAMPLE 13

Dissolution Profile of the Bioadhesive Granules Obtained as per Examples 1 and 2

Dissolution tests were carried out in accordance with the following test conditions:

apparatus: USP Ed. XXII, Apparatus II pp. 1578–1579
dissolution medium: phosphate buffer pH 5.9–900 ml
temperature: 37° C.
stirring speed: 50 rpm
detection: UV absorption of 282 nm

TABLE 2

| Time    | % Furosemide Released |            |            |            |
|---------|------------|------------|------------|------------|
| (hours) | Example 1a | Example 1b | Example 2a | Example 2b |
| 0       | 0          | 0          | 0          | 0          |
| 1       | 25.1       | 26.2       | 28.0       | 16.0       |
| 2       | 37.3       | 36.2       | 48.2       | 36.8       |
| 4       | 48.6       | 46.4       | 57.2       | 49.6       |
| 8       | 60.3       | 58.2       | 71.5       | 61.3       |
| 12      | 67.1       | 66.2       | 83.5       | 71.4       |
| 18      | 72.3       | 71.0       | 93.1       | 84.4       |
| 24      | 77.3       | 79.3       | 99.6       | 94.8       |

The table shows that the same active ingredient can have different release profiles when different components and microunits are used

EXAMPLE 14

Dissolution Profile of the Bioadhesive Granules Obtained as per Example 3

Dissolution tests were carried out in accordance with the following test conditions:

apparatus: II USP Ed. XXII as per Ex. 13.
dissolution medium: 0.1N HCl - 900 ml
temperature: 37° C.

stirring speed: 50 rpm
determination: HPLC (high performance liquid chromatography)
column: Novapack C18
mobile phase:
  acetonitrile=60
  acetate buffer pH 4.5=40
flow: 1.2 ml/min
detector: UV 225 nm
temperature: 25° C.
internal standard: nortriptyline

TABLE 3

| Time | % Terfenadine Released | | |
|---|---|---|---|
| (hours) | Example 3a | Example 3b | Example 3c |
| 0 | 0 | 0 | 0 |
| 1 | 31.0 | 43.9 | 37.6 |
| 2 | 46.1 | 59.7 | 50.5 |
| 4 | 55.5 | 71.9 | 66.5 |
| 8 | 67.5 | 84.3 | 84.2 |
| 12 | 76.1 | 91.6 | 91.4 |
| 18 | 84.0 | 97.9 | 98.4 |
| 24 | 92.9 | 100.0 | 100.0 |

In all the Table 3 formulations the active ingredient is released in a controlled way over 24 hours.

EXAMPLE 15

Evaluation of Bioadhesive Properties

To evaluate in vitro the bioadhesive properties of the formulations which are an object of the present invention, a method permitting evaluation of bioadhesive properties directly on finished dosage forms (G. Sala et al., *Proceed. Iny. Symp. Contr. Rel. Bioact. Mat.*, 16:420, 1989) was used. (A tensile tester made by INSTRON, Canton, Mass. is also a suitable apparatus for assessing bioadhesive strength.) This evaluation was based on measurements of the flow of water required to remove the granules from the intestinal mucous membrane of a rabbit. A strip of rabbit mucous membrane is placed horizontally in a suitable temperature-controlled chamber set at 37° C. The tissue is first washed with predetermined volumes of water (e.g. 20–30 ml) by means of a peristaltic pump. An exact quantity of granules by weight (e.g. 5–15 mg) is then placed on the tissue and allowed to stand for 2 minutes to ensure proper hydration of the granule bioadhesive coat. The granules are then eluted with water pumped by a peristaltic pump for 10 minutes. The washed-away granules are collected and the active ingredient content is determined by U.V. assay in order to establish the exact percentage of particles removed. Subsequent tests are carried out using increasing eluting flows. The results are shown in Table 4, where the percentages of removal at the different water flows are listed respectively for:

A: granules containing furosemide with no coating of bioadhesive material (average diameter 300–500 microns);

B: granules containing furosemide prepared as described in Example 1a (average diameter 400–600 microns).

TABLE 4

| Flow | % Granules Removed | |
|---|---|---|
| (ml/min) | A | B |
| 6.0 | 76.9 | 0.0 |
| 7.1 | 88.1 | 0.0 |
| 15.7 | 100.0 | 17.9 |
| 17.7 | 100.0 | 26.6 |
| 19.8 | 100.0 | 33.5 |
| 21.7 | 100.0 | 39.7 |

From Table 4, it is evident that under the same elution conditions, the presence of a bioadhesive coating will significantly reduce the quantity of granules removed from the mucous membrane.

EXAMPLE 16

Effect of Changing the Bioadhesive Coat Thickness on Units for the Controlled Release of Furosemide A demonstration of the effect of the bioadhesive coating thickness on dissolution and bioadhesion values was obtained preparing 3 different formulations using the controlled-release nucleus described in Example 2a, but changing the proportions of the ingredients which make up the bioadhesive coating of Example 2a:

| Formulation A: | |
|---|---|
| Controlled release granules | 50 parts |
| Acrylic acid copolymer | 25 parts |
| Hydroxypropylmethylcellulose | 25 parts |
| Formulation B: | |
| Controlled release granules | 33 parts |
| Acrylic acid copolymer | 33 parts |
| Hydroxypropylmethylcellulose | 33 parts |
| Formulation C: | |
| Controlled release granules | 20 parts |
| Acrylic acid copolymer | 40 parts |
| Hydroxypropylmethylcellulose | 40 parts |

TABLE 5

| Comparative Dissolution of Formulations A, B and C | | | |
|---|---|---|---|
| Time | % Furosemide Dissolved | | |
| (hours) | A | B | C |
| 1 | 36.4 | 28.0 | 16.0 |
| 2 | 54.1 | 48.2 | 36.8 |
| 3 | 62.7 | 56.2 | 45.7 |
| 5 | 73.2 | 63.0 | 53.0 |
| 8 | 82.7 | 71.5 | 61.3 |
| 12 | 88.7 | 83.5 | 71.4 |

TABLE 5-continued

Comparative Dissolution of Formulations A, B and C

| Time (hours) | % Furosemide Dissolved | | |
|---|---|---|---|
| | A | B | C |
| 18 | 91.9 | 93.1 | 84.4 |
| 24 | 93.3 | 99.6 | 94.8 |

TABLE 6

Comparative Evaluation of the Bioadhesive Properties of Formulations A, B and C

| Flow (ml/min) | % Granules Removed | | |
|---|---|---|---|
| | A | B | C |
| 15.7 | 17.3 | 12.2 | 4.5 |
| 17.7 | 25.6 | 13.5 | 6.4 |
| 19.8 | 33.0 | 16.7 | 8.9 |
| 21.7 | 39.0 | 17.2 | 11.2 |

The Table 5 and 6 data show that it is possible to improve bioadhesion by increasing the thickness of the bioadhesive coat without significantly affecting the dissolution profile of the active ingredient. This in turn means that in accordance with the invention each of bioadhesion and release control can be modulated separately without substantial mutual influence.

EXAMPLE 17

Effect of Changing the Bioadhesive Coat Thickness on Microunits for the Controlled Release of Terfenadine A demonstration of the effect of the bioadhesive coating thickness on dissolution and bioadhesion values was obtained preparing three different formulations the controlled-release nucleus of which was prepared as described in Example 3a), but the proportions of the ingredients which make up the bioadhesive coating were changed in accordance with the same method described in Example 16 (formulations D, E and F):

TABLE 7

Comparative Dissolution of Formulations D, E and F

| Time (hours) | % Terfenadine Released | | |
|---|---|---|---|
| | D | E | F |
| 1 | 36.5 | 31.5 | 34.6 |
| 2 | 47.2 | 46.1 | 50.5 |
| 4 | 60.5 | 55.5 | 62.5 |
| 8 | 71.3 | 67.5 | 74.2 |
| 12 | 83.9 | 76.1 | 81.4 |
| 18 | 88.0 | 84.0 | 89.5 |
| 24 | 95.0 | 92.9 | 98.1 |

TABLE 8

Comparative Evaluations of the Bioadhesive Properties of Formulations D, E and F

| Flow (ml/min) | % Granules Removed | | |
|---|---|---|---|
| | D | E | F |
| 11.4 | 17.6 | 0.0 | 0.0 |
| 15.7 | 19.1 | 7.6 | 5.5 |
| 19.8 | 31.1 | 11.6 | 6.3 |
| 21.7 | 35.1 | 16.5 | 12.1 |

Again, Table 7 and 8 data show that it is possible to improve bioadhesion by increasing the thickness of the bioadhesive coat without significantly affecting the dissolution profile of the active ingredient.

EXAMPLE 18

Effects of the Compression Force and Crumbling Method

The bioadhesive and dissolution properties of the present invention are not dependent on the compression force used for dry coating the controlled release units with bioadhesive polymers and are equally not dependent on the crumbling method used.

To prove this, three formulations were prepared as described in Example 2a. These formulations contained furosemide and differed from each other either because of a different compression force used during compression of the bioadhesive polymers or because of the crumbling method:

Formulation G:
  Compression force used 1.5 KN
  Mechanical crumbling by an Erweka apparatus
Formulation H:
  Compression force used 7 KN
  Mechanical crumbling by an Erweka apparatus
Formulation I:
  Compression force used 7 KN
  Gentle crumbling by hand in a mortar

TABLE 9

Dissolution of Formulations G, H and I

| Time (hours) | % Furosemide Released | | |
|---|---|---|---|
| | G | H | I |
| 1 | 37.6 | 36.5 | 35.9 |
| 2 | 47.3 | 45.2 | 49.3 |
| 4 | 60.7 | 60.6 | 62.9 |
| 8 | 79.3 | 76.3 | 80.3 |
| 12 | 92.5 | 93.9 | 94.7 |
| 18 | 100.0 | 100.0 | 100.0 |

TABLE 10

Evaluation of the Bioadhesive Properties of Formulations G, H and I

| Flow (ml/min) | % Granules Removed | | |
|---|---|---|---|
| | G | H | I |
| 13.7 | 4.2 | 5.7 | 5.3 |
| 15.7 | 6.5 | 6.9 | 7.1 |
| 19.8 | 9.0 | 11.1 | 10.8 |

The Table 10 data show how small are the differences in dissolution and bioadhesion values observed when changing either the compression force or the crumbling method.

What is claimed is:

1. A controlled release mucoadhesive pharmaceutical composition comprising a plurality of individually coated microunits detached from one another, said coated microunits having an external diameter within the range between about 125 and about 2500 microns, each of said microunits comprising:

a core comprising at least one pharmaceutically active ingredient and a polymer film coating means for controlling the release of said active ingredient from said core, said core having substantially no mucoadhesive properties prior to coating;

a non-swollen mucoadhesive polymeric coating substantially completely enveloping said core and detached from mucoadhesive polymeric coatings of other microunits, said coating comprising at least one physiologically acceptable bioadhesive polymer in an amount sufficient to impart to said coated microunits a predetermined ability to adhere to a mucus membrane, wherein said mucoadhesive coating is applied to said core in a dry-tabletting process wherein said core is coated by said mucoadhesive;

wherein the weight ratio of said core to said coating is within the range between about 5:1 and about 1:10; and wherein said polymer film coating means for controlling the release of said active ingredient has been preselected to yield, together with any release control function contributed by said coating, a predetermined controlled release profile for the coated microunits.

2. The composition according to claim 1, wherein said bioadhesive coating has an outer mucoadhesive surface, said composition further comprising at least one physiologically acceptable excipient in contact with said outer surface.

3. The composition according to claim 1, wherein said means for controlling the release of the active ingredient are selected from the group consisting of matrix, reservoir, osmotic and biodegradable release control materials and combinations thereof.

4. The composition according to claim 1, wherein the mucoadhesive polymer is selected from the group consisting of acrylic polymers, cellulose derived polymers, natural polymers having mucoadhesive properties, and mixtures of at least two of the foregoing.

5. The composition according to claim 1 wherein the mucoadhesive polymer is selected from the group consisting of carbomers, polycarbophils, hydroxypropylmethylcelluloses, hydroxypropylcelluloses and mixtures of at least two of the foregoing.

6. The composition according to claim 1, wherein said coating comprises said mucoadhesive polymer and a second polymer acting as a binder.

7. The composition according to claim 6, wherein the weight ratio of said mucoadhesive polymer to said binder is within the range of about 0.2 and about 20.

8. The composition according to claim 7, wherein said range is between about 0.5 and about 5.

9. The composition according to claim 1, wherein the weight ratio of said cores to said polymeric coating is within the range between about 2.5 and about 0.25.

10. The composition according to claim 1, wherein said diameter is within the range between about 300 and about 600 microns.

11. The composition according to claim 2, said composition being suitable for oral administration, wherein said excipient comprises at least one hydrophobic agent that delays hydration of the mucoadhesive coating and at least one disintegrating agent that promotes dispersion of the mucoadhesive microunits over the gastrointestinal mucous membrane.

12. The composition according to claim 11, wherein the hydrophobic agent is selected from the group consisting of magnesium stearate, calcium stearate, talc and combinations thereof.

13. The composition according to claim 11, wherein the disintegrating agent is selected from the group consisting of cross linked polyvinylpyrrolidone, carboxymethyl starch, croscarmellose sodium starch and combinations thereof.

14. The composition according to claim 11, wherein the weight percentage of the hydrophobic agent is within the range of about 1 to about 10% and that of the disintegrating agent is within the range of 2 to 20%, said weight percentages being based on the weight of the entire composition.

15. The composition according to claim 1, wherein the active ingredient is selected from the group consisting of analgesic, antibacterial, antibiotic, anticonvulsant, antidepressant, antidiabetic, antifungal, antihistaminic, antihypertensive, anti-inflammatory, antiparkinsonian, antipyretic, anticholinergic, antimicrobial, antiviral, antiulcerative, bronchodilating, cardiovascular, contraceptive, decongestant, diuretic, hypoglycemic, hormonal, ophthalmic, hypnotic, sympathomimetic, tranquilizing drugs and vitamins.

16. The composition according to claim 1, wherein said active ingredient is selected from the group consisting of furosemide, terfenadine, calcitonin, naproxen, pilocarpine and tetracycline hydrochloride.

17. A process for preparing a pharmaceutical composition according to claim 1, comprising the steps of:

a) mixing controlled release core particles containing at least one pharmaceutically active ingredient and having no mucoadhesive properties with a polymer or polymer mixture having mucoadhesive characteristics, b) dry-compressing the mixture so obtained to cause said mucoadhesive polymer or mixture to bind to the core particles on the surface thereof;

c) crumbling the resulting compressed mass to form microunits individually coated with said mucoadhesive polymer being detailed from one another;

d) selecting a multiplicity of said microunits of a size in the range of about 1 to about 2500 microns to form said composition.

18. The process according to claim 17, further comprising combining said microunits with a physiologically acceptable carrier or excipient.

19. A method for designing a controlled-release mucoadhesive dosage form comprising individually coated microunits detached from one another, said microunits comprising a therapeutically active ingredient, the method comprising the steps of:

(i) selecting a predetermined controlled-release profile and a predetermined mucoadhesive strength for the dosage form to be designed;

(ii) preparing core microparticles containing said active ingredient and polymer film coating means for controlling the release of the active ingredient, wherein said polymer film coating means for controlling release has been pre-selected to yield, together with any release control function contributed by a coating in step (iv) below, said predetermined controlled release profile, and wherein said microparticles have substantially no mucoadhesive properties;

(iii) assessing the controlled release profile of said core microparticles;

(iv) coating each of said microparticles with a coating comprising at least one non-swollen mucoadhesive polymer in a dry tabletting process, to form said dosage form, wherein the weight ratio of said microparticles to said coating is within the range between about 5:1 and 1:10, said coating being in an amount sufficient to confer said predetermined mucoadhesive strength to said microparticles; and (v) assessing the mucoadhesive strength of said dosage form.

20. A controlled release mucoadhesive pharmaceutical composition comprising a plurality of individually coated microunits detached from one another, said coated microunits having an external diameter within the range between about 125 and about 2500 microns, each of said microunits comprising:

a core comprising at least one pharmaceutically active ingredient and polymer film coating means for controlling the release of said ingredient from said core, said core having substantially no mucoadhesive properties prior to coating;

a non-swollen mucoadhesive polymeric coating substantially completely enveloping said core and detached from mucoadhesive polymeric coatings of other microunits, said coating comprising at least one physiologically acceptable bioadhesive polymer in an amount sufficient to impart to said coated microunits a predetermined ability to adhere to a mucus membrane, wherein said mucoadhesive coating is applied to said core in a dry-tabletting process wherein said core is coated by said mucoadhesive;

wherein the weight ratio of said core to said coating is within the range between about 5:1 and about 1:10, and wherein said polymer film coating means controlling the release of said active ingredient has been preselected to yield a predetermined controlled release profile for the coated microunits, said coating having essentially no effect on said release profile.

21. A method for designing a controlled-release mucoadhesive dosage form comprising individually coated microunits detached from one another, said microunits comprising a therapeutically active ingredient, the method comprising the steps of:

(i) selecting a predetermined controlled-release profile and a predetermined mucoadhesive strength for the dosage form to be designed;

(ii) preparing core microparticles containing said active ingredient and polymer film coating means for controlling the release of the active ingredient, wherein said polymer film coating means for controlling release has been pre-selected to yield said pre-determined control release profile and wherein said microparticles have substantially no mucoadhesive properties;

(iii) assessing the controlled release profile of said core microparticles;

(iv) coating each of said microparticles with a coating comprising at least one non-swollen mucoadhesive polymer to form said dosage form, wherein the weight ratio of said microparticles to said coating is within the range between about 5:1 and 1:10, said coating being in an amount sufficient to confer said predetermined mucoadhesive strength to said microparticles and having essentially no effect on said release profile, wherein said mucoadhesive coating is applied to said core in a dry-tabletting process wherein said core is coated by said mucoadhesive; and (v) assessing the mucoadhesive strength of said dosage form.

22. A controlled release mucoadhesive pharmaceutical composition comprising a plurality of individually coated microunits detached from one another, said coated microunits having an external diameter within the range between about 125 and about 2500 microns, each of said microunits comprising:

a core comprising at least one pharmaceutically active ingredient and a polymer film coating means for controlling the release of said active ingredient from said core, said core having substantially no mucoadhesive properties prior to coating;

a dry mucoadhesive polymeric coating substantially completely enveloping said core and detached from mucoadhesive polymeric coatings of other microunits, said coating comprising at least one physiologically acceptable bioadhesive polymer in an amount sufficient to impart to said coated microunits a predetermined ability to adhere to a mucus membrane, wherein said mucoadhesive coating is applied to said core in a dry-tabletting process wherein said core is coated by said mucoadhesive;

wherein the weight ratio of said core to said coating is within the range between about 5:1 and about 1:10, and wherein said polymer film coating means for controlling the release of said active ingredient has been preselected to yield, together with any release control function contributed by said coating, a predetermined controlled release profile for the coated microunits.

23. A method for designing a controlled-release mucoadhesive dosage form comprising individually coated microunits detached from one another, said microunits comprising a therapeutically active ingredient, the method comprising the steps of:

(i) selecting a predetermined controlled-release profile and a predetermined mucoadhesive strength for the dosage form to be designed;

(ii) preparing core microparticles containing said active ingredient and polymer film coating means for controlling the release of the active ingredient, wherein said polymer film coating means for controlling release has been pre-selected to yield, together with any release control function contributed by a coating in step (iv) below, said predetermined controlled release profile, and wherein said microparticles have substantially no mucoadhesive properties;

(iii) assessing the controlled release profile of said core microparticles;

(iv) coating each of said microparticles with a coating comprising at least one dry mucoadhesive polymer, to form said dosage form, wherein the weight ratio of said microparticles to said coating is within the range between about 5:1 and 1:10, said coating being in an amount sufficient to confer said predetermined mucoadhesive strength to said microparticles, wherein said mucoadhesive coating is applied to said core in a dry-tabletting process wherein said core is coated by said mucoadhesive; and (v) assessing the mucoadhesive strength of said dosage form.

* * * * *